May 12, 1964 E. C. BERNHARDT Plant Pat. 2,403
AVOCADO TREE
Filed June 18, 1962
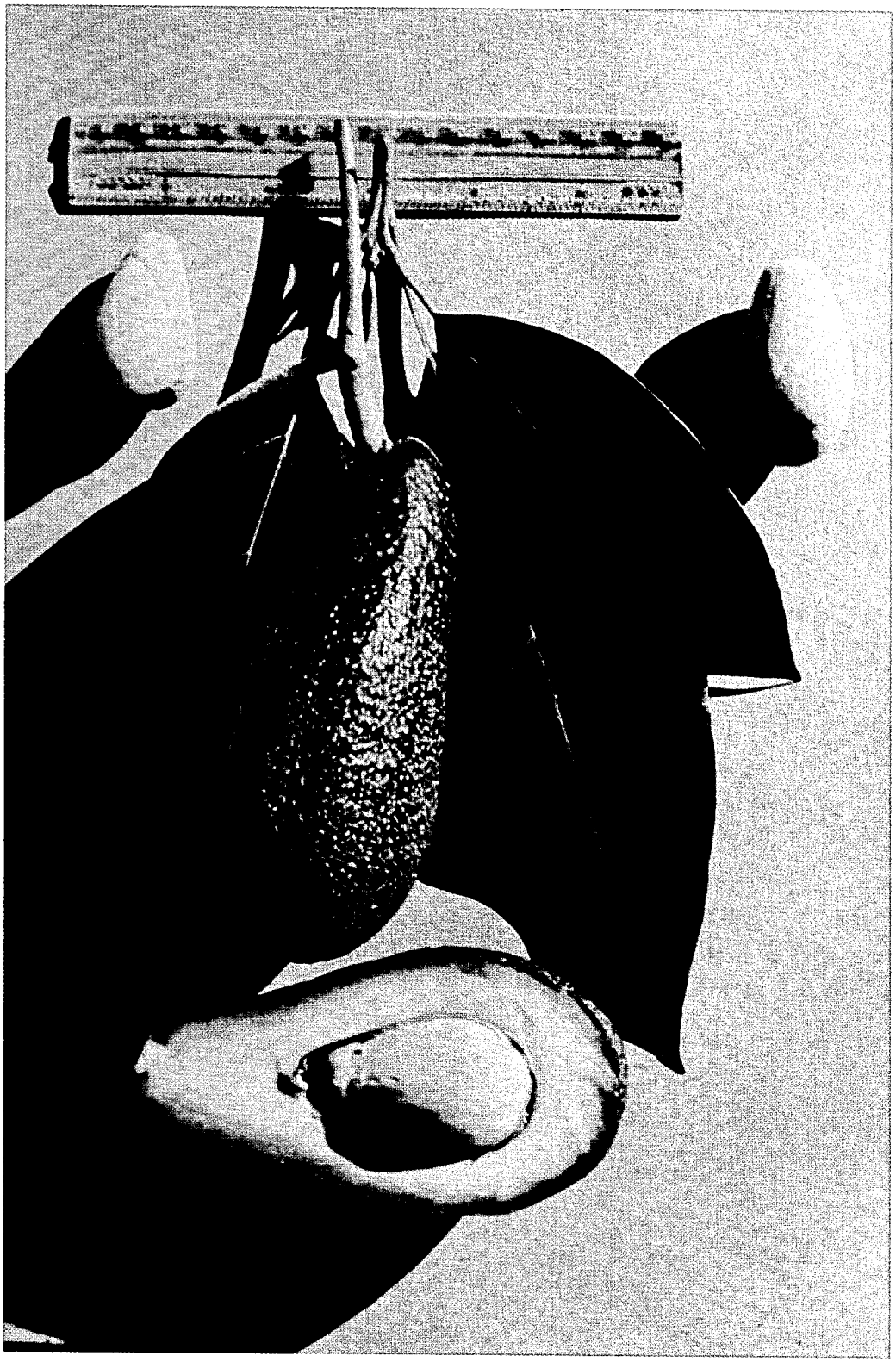
Inventor
Edwin C. Bernhardt United States Patent Office Plant Pat. 2,403
Patented May 12, 1964

2,403
AVOCADO TREE

Edwin C. Bernhardt, 4275 Foothill Road, Ventura, Calif.

Filed June 18, 1962, Ser. No. 203,417
1 Claim. (Cl. Plt.—44)

My invention relates to a new and distinct fall bearing variety of avocado tree which is an improvement over previously known fall-bearing varieties. The tree produces excellent small-sized marketable fruits that mature during October and November.

The original tree is an intentional cross developed by me by hand pollination and isolation of a Fuerte variety (unpatented) tree upon my own property located at Santa Paula, California. The pollen for this hybrid cross was obtained from an un-named but known (unpatented) fall bearing thin skinned variety of avocado tree. The hybrid cross seed was planted in a nursery at the same location, May 1954, and the hybrid cross tree was about 16 inches high in October 1954; it was planted in a cultivated tree row with other avocado trees at the same location.

This hybrid cross has been an early bearer of avocado fruits. It produced three fruits at two years of age, fifty-four fruits at three years of age, one hundred and twenty-nine fruits at four years of age, five fruits at five years of age, and three hundred and twenty-eight fruits at six years of age. Graftwood removed from this parent tree for the last two years has reduced fruiting.

The tree bears a small to medium-sized fruit that matures in October and November. This is particularly good since at this time of the year there are few, if any, desirable maturing avocado fruit. The tree has strong growth habits and the general appearance of the fruit is excellent like the Fuerte (unpatented) but is smaller. The fruit holds on the tree well and ripens uniformly to full maturity of the fruit.

Desirable characteristics of the tree are present under typical avocado orchard growing conditions. Characteristics of the tree and fruit vary slightly under various conditions of climate, moisture, topography, soil and care.

This hybrid cross variety has been successfully asexually reproduced by grafting and budding on Mexican family seedlings including Topa Topa, Ganter and Duke (all unpatented thin-skinned varieties). Also, thirty-four year old trees topworked to this hybrid cross variety are producing large crops of fruit identical to that fruit harvested from the mother tree (original hybrid cross). This asexual reproduction was done by me on my property located at Santa Paula, California. Tip grafts and buds have grown rapidly and the young terminal branches are slightly speckled.

The terminal foliage as well as the fruit stem and button of this new variety of avocado is illustrated in the appended color photograph which also includes illustrations showing the manner in which the seed is positioned in the fruit, the thickness of the skin, the seed skin, the seed cavity and the general appearance of the seed.

THE TREE

*Growth Habits*

The tree is more upright than spreading, having its main frame branches growing out from the trunk and substantially at right angles to the trunk.

The tree is about ten feet high (at six and one-half years), appears to have a strong root system and is characterized by new and strong branch growth after each irrigation.

*Bearing Habits and Blossoming*

In the intermediate climate zone of Ventura County the subject variety blossoms in February and March.

Usually over one-half of the blooms will set fruit in April or before. The fruit reaches full size in about eight and one-half months and will hang on the tree past the middle of the following January with only slight fruit drop.

*Hardiness*

No claims are made here to indicate that the tree will withstand temperatures below 26° Fahrenheit for more than a few hours at a time. However, it has been determined that the tree will stand cold conditions about the same as the Fuerte (unpatented) variety.

*Maturity*

The tip-grafted or budded trees start bearing in two to three years. This variety of tree appears to be early bearing somewhat like the Rincon (unpatented) variety.

*Fruit Placement*

The fruit is distributed throughout the tree. The fruit does not always set in clusters but frequently two fruit hang side by side upon a forked stem. As the fruit matures the stems turn from a green to a yellowish light green color. The stems of the fruit vary in length from about two inches to about five inches.

*Ripening Date*

In Ventura County along the westerly edge of the intermediate zone, the fruit usually matures (above 8% oil content) from October 15 to November 30. The fruit will remain on the tree until about January 15 with fewer than ten percent of fruit falling. The fruit reaches at least ten percent oil content by October 15. By January 15 the fruit has over sixteen percent oil content.

*Foliage*

*Quantity.*—The foliage is abundant in spring and in early summer and under normal conditions less than one-tenth of the leaves drop when a heavy load of fruit is being carried and when blooming season approaches.

*Color.*—The upper surfaces of mature leaves are semi-glossy dark green and the lower surfaces are a dull green with a grayish cast. The upper surfaces of immature leaves are light tan and glossy green and the lower surfaces are a light green with light gray cast. The color of mature leaves varies during the different seasons and soil moisture and fertility.

*Size.*—The mature leaves are elongated, having a length of about six to eight inches and a width of about two inches to two and one-half inches.

*Shape.*—Normal, with edges slightly waved or rippled.

*Texture and veining.*—The leaves are thinner than those of the Fuerte (unpatented) variety and are not puckered. The principal leaf veins and stems are lighter green in color than the remainder of the leaf. The principal leaf veins are pronounced while the minor leaf veins are not very distinct. The leaves have six to ten ribs with the midrib nearly straight, and other ribs are alternately placed and emanating from midrib.

*Distribution.*—The leaves are well distributed over the tree and some of the branches form a skirt toward the ground.

THE FRUIT

*Weight*

The fruit from this hybrid cross tree weighs between seven and nine ounces; the average fruit will weigh about seven to eight ounces.

*Shape*

The fruit has a nearly symmetrical pear shape and measures about 3½ inches to five inches in length and about one and three-quarter inches to two inches in diameter. The area at the stem end of the fruit is small but not pointed. There is a tendency for a few of the fruits to crook their necks slightly. The photograph indicates the shape of the fruit; the fruit selected being typical of all fruit found on the tree.

*Skin*

The color of the skin is common to the green Mexican varieties. The skin is medium green, see photograph, speckled with very light yellowish-green specks or oil pores that are fewer and farther apart at the stem end as compared with the bloom end where they are progressively closer together and greater in number. The medium green background color becomes (at maturity) a little darker at the bloom end but never rots or cracks. Some of the fruit have a slightly pebbled skin. A roughened or rust condition does not appear on the skin.

*Aspect*

As the period of maturity approaches, the skin loses some of its gloss and turns to a dull medium green color.

*Texture*

The skin of this fruit has about the same thickness as the Fuerte (unpatented) variety. The skin is leathery, tough and pliant like the Fuerte (unpatented) variety, and is not woody like the Hass (expired Plant Patent No. 139). The skin adheres to the fruit flesh enough to prevent sagging, checking and breaking out; however, the skin peels and lifts easily away from the fruit flesh at maturity.

*Button*

The button is medium sized and partly buried in a slight depression located off-center from the longitudinal axis of the fruit. The button remains in the fruit when the stem is clipped. Relatively high winds do not blow these fruits off the tree.

*Flesh*

*Color.*—The flesh is a rich light yellow, see photograph, abruptly blending into a thin rim of light green flesh near the skin.

*Flavor.*—The flavor is slightly milder than the Fuerte (unpatented) variety and is rated very good to excellent.

*Texture.*—The flesh texture is firm, ripens uniformly and has unusually good storage qualities. The flesh has a butter-like consistency with practically no fiber content.

*Oil content.*—The flesh reaches at least ten percent oil by October 15. The commissioner of the California Department of Agriculture, Santa Paula, California, measured the oil content of the fruit to be thirteen to over sixteen percent at time of maturity.

*Seed*

*Shape.*—The seed is pear shaped, having the apex end usually blunt. The coat of the seed extends to a point at the apex end and fills the seed cavity. The average seed weight has been about six-tenths of an ounce. The average ratio of seed weight to flesh weight for one hundred and twenty-nine fruits tested was 9.2 percent. Each seed averaged about six-tenths of an ounce.

*Color and texture* (see photograph).—The seed is light yellow in color and has a slightly wavy slick surface. The seed is hard and starchy but can be cut by a knife or pried into two distinct halves.

*Seed coat.*—The seed coat is light brown when the seed is mature and is relatively thin. It adheres to the seed and not to the flesh when the seed is removed from the flesh.

Having thus described my invention, I claim:

The new and distinct variety of avocado tree, substantially as herein shown and described, distinguished as to novelty by its ripening period in the fall; medium to small-sized fruits having its medium green skin background speckled light yellowish green oil pores when fruits are fully matured; having a skin that is medium thick and peels easily from the flesh; the fruits borne on short length stems; the fruits having a small size seed that does not adhere to the meat flesh, and rich light yellow flesh changing abruptly to a small band of light green near the skin, has practically no fibre and has a mild butterlike consistency.

No references cited.